United States Patent [19]

Schlein

[11] Patent Number: 4,730,608

[45] Date of Patent: Mar. 15, 1988

[54] EXTERNAL BONE-ANCHORING FIXATOR

[76] Inventor: Allen P. Schlein, 107 Curtis Ter., Fairfield, Conn. 06432

[21] Appl. No.: 836,538

[22] Filed: Mar. 5, 1986

[51] Int. Cl.⁴ ............................................. A61F 5/04
[52] U.S. Cl. ............................ 128/92 Z; 128/92 ZW; 128/92 ZK
[58] Field of Search ..................................... 128/92 Z

[56] References Cited

U.S. PATENT DOCUMENTS

| | | | |
|---|---|---|---|
| 2,391,537 | 12/1945 | Anderson | 128/92 Z |
| 2,391,693 | 12/1945 | Ettinger | 128/92 Z |
| 4,258,708 | 3/1981 | Gentile | 128/92 Z |
| 4,273,116 | 6/1981 | Chiquet | 128/92 Z |

OTHER PUBLICATIONS

Catalogue of Richards Medical Company—"Richards External Fixation Systems," Copyright 1983.
Catalogue of EBI Medical Systems, Inc.—"Dynamic Axial Fixation," covers and p. 1, date unknown.
Zimmer brochure—"Fracture Management Systems," undated.

Primary Examiner—Gregory E. McNeill
Attorney, Agent, or Firm—Spencer E. Olson

[57] ABSTRACT

A fixator for externally anchoring broken bones including a pair of generally planar members each having a plurality of openings adapted to receive a respective group of bone pins inserted in respective pieces of bone. The pins are clamped to the planar members with respective headed screws, and the members are held in adjustable end-to-end relationship by a lead screw anchored at one end in one of the members and engaging a threaded bore in the other member. In an embodiment useful for the treatment of comminuted displaced fractures of the distal radius and ulna, the said one member consists of two articulated sections arranged for angular and rotational adjustment. The lead screw extends beyond the distal end of the said other member and its free end is of the same shape and size as the heads of the clamping screws, and of other screws provided for locking the planar members in adjusted relative positions, enabling longitudinal adjustment and loosening and tightening of all screws to be done with a single tool, preferably an easily manipulated knurled wheel having an opening corresponding in shape and size to the screw heads.

14 Claims, 8 Drawing Figures

EXTERNAL BONE-ANCHORING FIXATOR

BACKGROUND OF THE INVENTION

This invention relates to an external boneanchoring element, or fixator.

External anchoring of bones is an old surgical technique which is particularly useful for long bones such as the femur, the tibia, the humerus, the radius, the cubitus and the bones in the leg. Available types of fixators enable two kinds of bone-anchoring to be carried out: non-transfixing anchoring, wherein pins are introduced into the bone without completely transversing it, and transfixing anchoring, which is mostly used on the leg and is more rigid than non-transfixing anchorage, wherein the pins traverse the bone and extend from one side of the limb to the other. In transfixing anchoring, two rods or frames fitted at both sides of the limb are anchored on two groups of pins disposed on either side of the fracture. The two frames or rods are stabilized by a brace interconnecting them, and may comprise sliding rods or bars, the length of which can be increased or reduced. Similar devices are used in non-transfixing anchoring, except, of course, the device is fitted at only that side of the fractured limb from which the pins extend.

External fixators of this general type commercially available from several companies, including EBI Medical Systems, Inc., Zimmer and Richards Medical Company, structurally are relatively complex and correspondingly costly to manufacture, and of those known to applicant, are inconvenient to use by reason of the need for a multiplicity of tools such as wrenches, including Allen wrenches of different sizes, in order to apply the fixator to the patient and/or to achieve compression/distraction adjustment.

Specialized versions of this type of external fixator for treatment of comminuted displaced fractures of the distal radius and ulna are also available from Richards ("Colles Fracture Frame") and Zimmer ("Clyburn Dynamic Colles Fixator"). Both devices immobilize the fractured distal radius by two holding pins in the metacarpal bones and two parallel pins in the radius, and each has a universal joint intermediate the two pairs of holding pins which may be adjusted to permit early motion of the wrist while still maintaining distraction and proper alignment of the fracture. However, partly because both employ a form of turnbuckle, application and adjustments of the Richards device involve the use of a hex wrench (Allen wrench with handle) and two open-end wrenches, and two knurled adjustng nuts and a hex wrench are involved in the adjustment of the Zimmer device. Both devices are complicated in their construction and manipulation and are, therefore, not only costly to manufacture but do not permit the convenient setting of the fracture nor the axial adjustment necessary to enable the bone fragments to be moved away or towards each other (retraction or compression).

SUMMARY OF THE INVENTION

The present invention seeks to obviate the above described disadvantages of currently available devices and to provide an external bone anchoring element which is simple in construction, easy to manufacture at relatively low cost, and easy and convenient to apply and adjust.

In accordance with the invention there is provided an external fixator formed of steam autoclavable materials, one embodiment of which is particularly useful on long bones, comprising first and second generally planar members formed of a plastics material which is machinable and/or moldable and steam autoclavable, such as Delrin, each having a plurality of bores adapted to receive pins which retain respective pieces of bone and to secure them to the two planar members. The planar members are held in adjustable end-to-end relationship by an elongated threaded rod anchored at one end in a first of the planar members and engaging a longitudinal threaded opening in the other planar member, and are maintained in a common plane by the threaded rod coacting with a second rod which is secured at one end to the first planar member and slidably engages a longitudinal opening in the other member which is parallel to but off-set from the threaded opening. Each pin-receiving bore is disposed transversely of the threaded rod and is provided with a sleeve or liner adapted to substantially match the diameter of the pins to the bore, and associated with each bore is a screw which extends inwardly from an edge of the planar member and threadably engages a respective sleeve for clamping a pin in the bore. All of the clamping screws and two locking screws disposed parallel to the clamping screws, one in each planar member for locking the adjusted positions of the members to the threaded rod, have a head of the same size and shape; the free end of the threaded rod has the same size and shape, thereby enabling longitudinal adjustment of the two members, and loosening and tightening of the clamping and locking screws to be done with a single simple tool. In the preferred embodiment, the tool is a knurled wheel having a central opening of the same shape and size as the screw heads, so as to be interchangeably used for the tightening or loosening of clamping and/or locking screws or adjusting the length of the fixator. The knurled wheel is easily manipulated with one hand thereby to leave the other hand free to support or guide the fixator. The rods, sleeves and the clamping and locking screws are all formed of a steam autoclavable metal, such as surgical stainless steel. The described construction enables the use of the fixator as a drill guide, or template, for fixing the bone pins to the fractured bone, thereby eliminating the need for the separate drill guides usually required with prior art fixators.

In other embodiments, useful for the treatment of comminuted displaced fractures of the distal radius and ulna, the planar members are somewhat smaller than in the above-described embodiment, and the first planar member is articulated at a point intermediate the anchored end of the threaded rod and the pin-receiving bores to enable angular adjustment in the plane of the member and/or relative rotation of the planar members to permit motion of the wrist while still maintaining distraction and proper alignment of the fracture. In common with the other embodiment, all longitudinal adjustment and tightening and loosening of screws is achieved with a single tool in the form of a simple knurled wheel.

BRIEF DESCRIPTION OF THE DRAWINGS

Other objects, features and advantages of the invention will be evident, and its construction and operation better understood, from the following description taken in conjunction with the accompanying drawings, in which.

DESCRIPTION OF THE PREFERRED EMBODIMENTS

Figure 1:
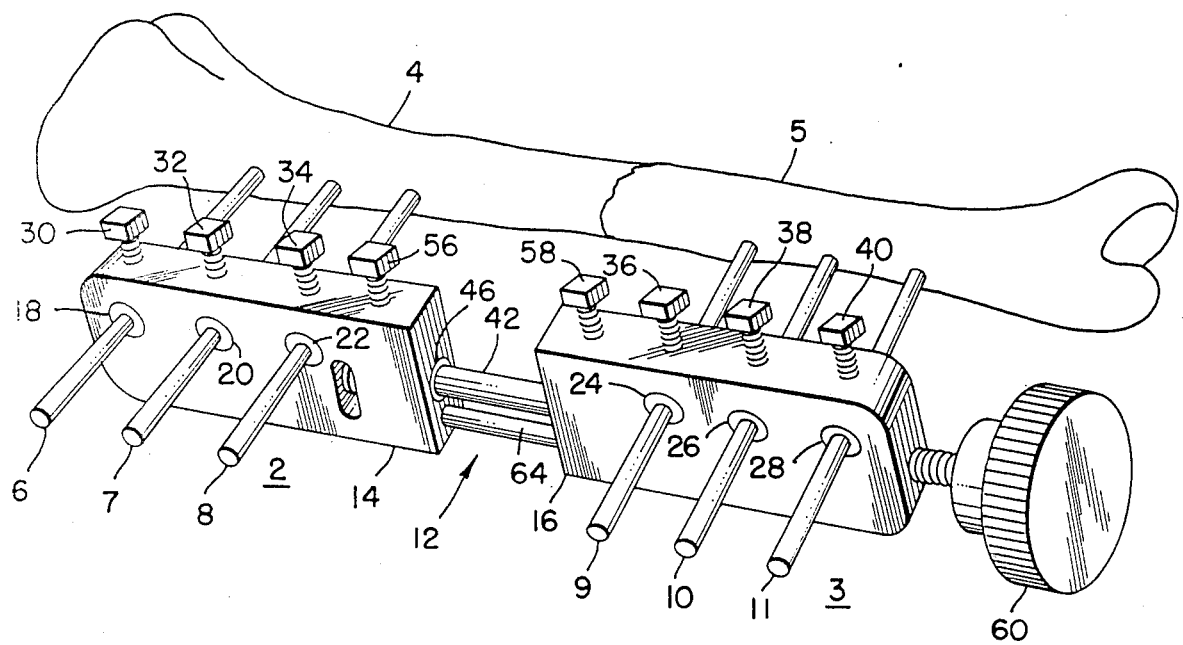
FIG. 1 is a perspective view of an external bone fixator shown holding and retaining two fragments of a fractured bone.
Figure 2:
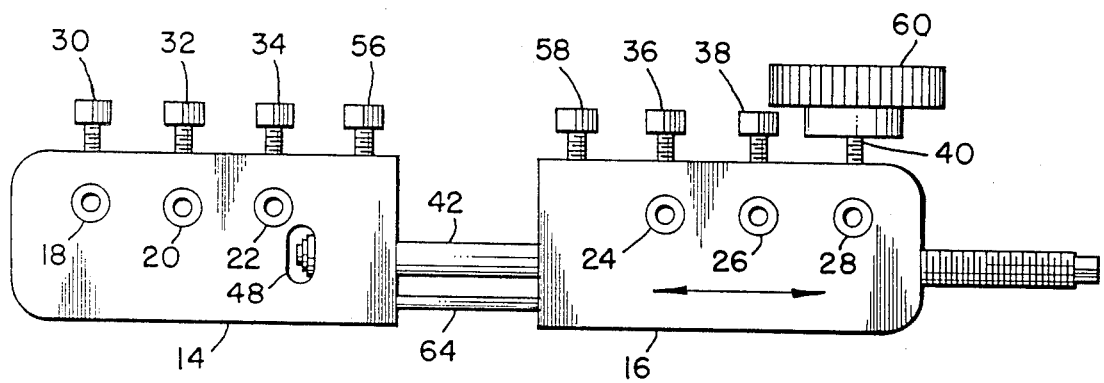
FIG. 2 is an elevation side view of the external fixture.

The external bone anchoring means illustrated in FIG. 1 comprises two groups of pins 2 and 3 and an external fixator 12 according to the invention for holding and retaining two bone fragments 4 and 5, respectively, relative to each other. The groups of pins 2 and 3 respectively comprise threaded nontransfixing, or half pins 6, 7, 8 and 9, 10, 11 which are screwed into the bone in conventional fashion with the aid of a tool, not shown. The inserted pins are disposed generally parallel to each other, and all are perpendicular to the long axis of the bone so as to lie in a common plane.

Figure 3:
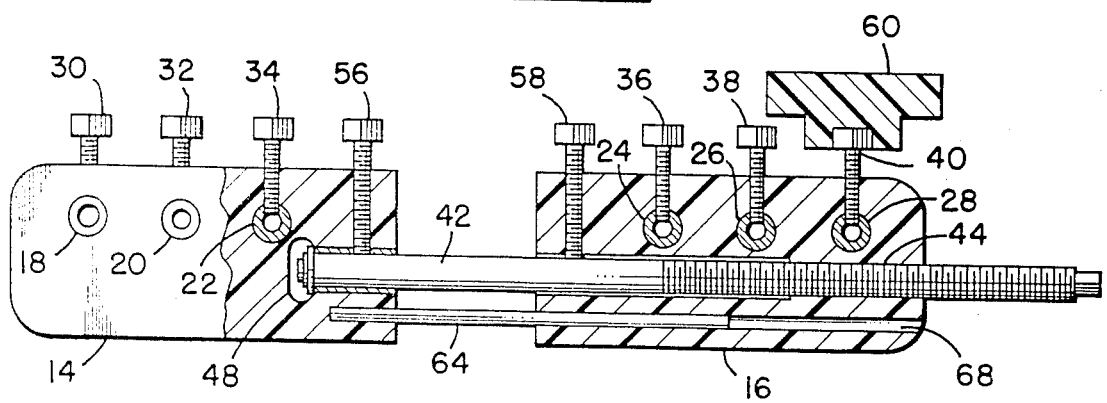
FIG. 3 is an elevation side view, partly in section, of the external fixator shown in FIG. 2.

The free ends of pins 6, 7, 8 of group 2 and pins 9, 10,11 of group 3 are clamped in respective bores which extend transversely through first and second planar members 14 and 16, respectively, each having the same rectangular cross-section, typically 1⅞ inches (4.76 cm) by ⅝ inch (1.59 cm) and each having a length of 3¾ inches (9.53 cm). The planar members may either be machined or molded from a machinable and/or moldable polymer plastics material which is also amenable to sterilization in a steam autoclave, such as Delrin. Each planar member has three transverse bores uniformly distributed along its length and disposed on a line displaced from its upper edge (as viewed in the Figures) by about ½ inch (1.27 cm), and each bore is provided with a lining or sleeve 18,20,22 and 24, 26, 28, respectively, received in the bore with a press fit, or alternatively, molded into the planar members, and having an inner diameter slightly larger than the diameter of the pins. Associated with each bore in member 14 is a square-headed screw 30, 32, 34, and associated with each bore in member 16 is a square-headed screw 36, 38, 40, all of which extend inwardly from the upper edge of their respective members and, as best seen in FIG. 3, threadably engage a respective sleeve for clamping a pin in the bore. The screws and sleeves preferably are formed of surgical stainless steel so as to be non-toxic and also sterilizable by steam autoclaving.

Figure 4:
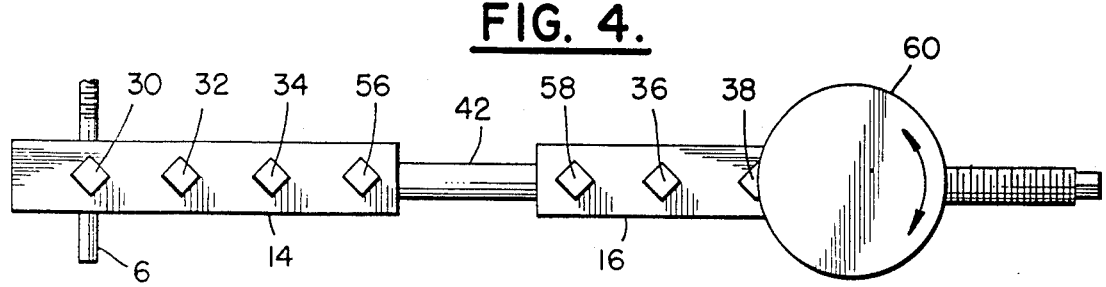
FIG. 4 is a top plan view of the fixator.
Figure 5:
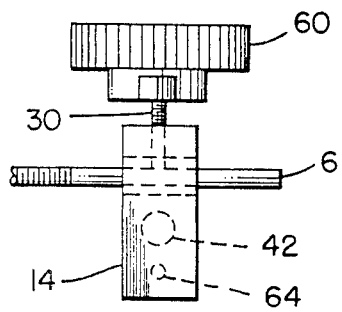
FIG. 5 is a left-end view of the fixator shown in FIGS. 2 and 3.
Figure 6:
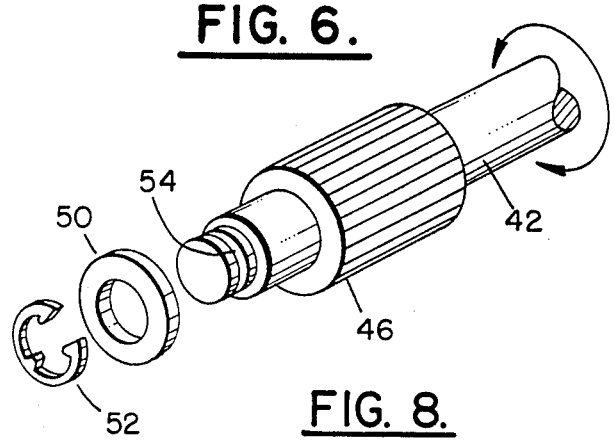
FIG. 6 is an enlarged, exploded view showing a structure for anchoring one end of the longitudinal adjustment rod.

The planar members 14 and 16 are maintained in adjustable end-to-end relationship by a rod 42, preferably stainless steel, anchored at one end in the end of member 16 which confronts the other member and over a major portion of its length threadably engages a partially threaded bore 44 formed in planar member 16. If desired, a threaded metal bushing, e.g., stainless steel, may be press-fitted in the bore for added strength, particularly in smaller-sized fixators. As seen in FIGS. 4 and 5, the diameter of rod 42 is about half the thickness dimension of the planar members, and it is disposed slightly below the aligned sleeves 18-28 and parallel to the top and bottom edges of the planar members. As best seen in FIGS. 3 and 6, one end of rod 42 is anchored in planar member 14 by coaction of a cylindrical metal (preferably stainless steel) sleeve 46 press-fitted in a longitudinal bore which terminates in an access opening 48 and having an inner diameter slightly larger than the diameter of rod 42, and a washer 50 having about the same outer diameter as sleeve 46 removably secured to a reduced-diameter end portion of rod 42 with a C-ring 52 which engages a circumferential groove 54 on the end portion. Unless locked by a square-headed locking screw 56 which extends inwardly from the upper edge of member 14 and threadably engages sleeve 46, rod 42 is adapted to rotate freely in the sleeve. The threaded portion of rod 42 is of sufficient length to enable longitudinal adjustment of member 16 relative to member 14 over a range of adjusted positions from a first position at which the confronting edges of the members are spaced about 3¼ inches (8.26 cm) apart to a second position at which the confronting edges contact each other. A square-headed threaded screw 58 extends inwardly from the upper edge of member 16 through a threaded opening for locking member 16 to adjusted positions along rod 42.

Rotation of threaded rod 42 to effect longitudinal movement of member 16 is simply and conveniently accomplished with a knurled wheel 60, also preferably formed of suitable machinable/moldable and sterilizable plastics material, such as Delrin, and typically 1¾ inches (4.45 cm) in diameter, having a square central recess or opening 62 dimensioned to receive the squared-off end of rod 42. The squared end of rod 42 is the same shape and size as the heads of all of the clamping and locking screws; thus, wheel 60 is the only tool required for effecting relative longitudinal adjustment of the planar members and loosening and tightening of the clamping and locking screws. The wheel is of a size to be easily manipulatd with one hand, thereby freeing the other hand to do other things.

Planar members 14 and 16 are normally maintained in the same plane by the coaction of rod 42 and a second smaller diameter rod 64, one end of which is anchored in an opening 66 in member 14, preferably by threading, and the other end of which is received with a sliding fit in a longitudinal bore 68 formed in member 16 in parallel off-set relationship with respect to rod 42. However, rod 64 is of such a length that it disengages from the bore 68 when member 16 is adjusted beyond the aforementioned first position (i.e., 3¼ inches spacing between the two members), thereby allowing the planar members to be rotated relative to each other about rod 42 and to be locked in a desired angularly adjusted relationship by tightening locking screws 56 and 58 against rod 42. This feature is of value in situations requiring relative axial rotation of bone fragments properly to treat the fracture.

It will be understood that the described embodiment is but one example of external fixator utilizing the principles of the invention and that fixators of this general configuration but of different sizes are possible and within the contemplation of the invention.

Figures 7, 8:
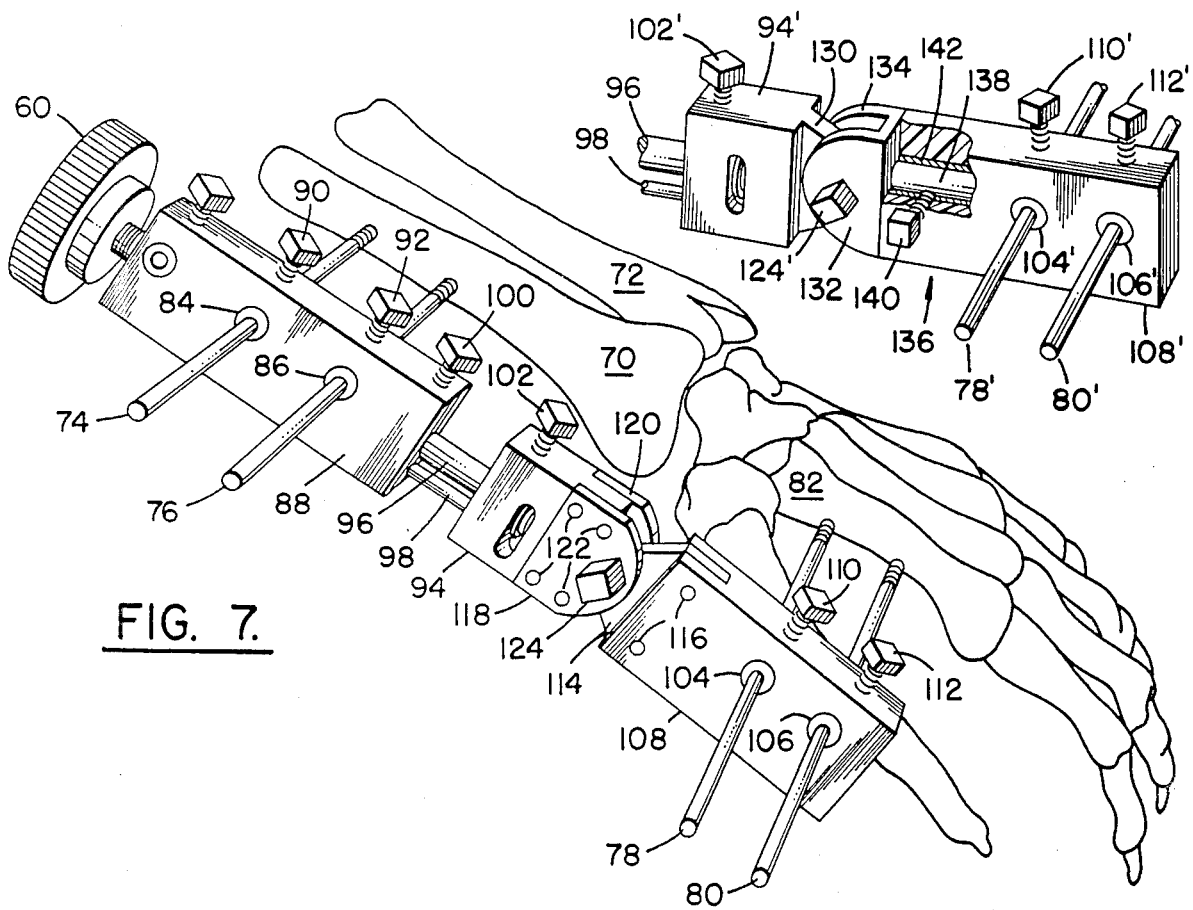
FIG. 7 is a perspective view of an articulated version of the fixator shown holding and retaining the metacarpal bones and the radius.
FIG. 8 is a perspective view of a portion of the fixator shown in FIG. 7 showing an alternative construction.

The external bone anchoring fixator illustrated in FIG. 7, useful for the treatment of comminuted displaced fractures of the distal radius 70 and ulna 72, is somewhat smaller than the above-described embodiment and is shown as engaging two pairs of pins 74, 76 and 78, 80 inserted into the radius and the metacarpals 82, respectively. The free ends of pins 74 and 76 are inserted in respective sleeves 84 and 86 molded or otherwise inserted in a first planar member 88 and clamped therein by respective square-headed clamping screws 90 and 92 which threadably engage a respective sleeve.

Planar member 88 is joined to a second planar member 94 by a rod 96 arranged to adjust the longitudinal displacement between them. The rod, preferably stainless steel, is anchored at one end in member 94 in the manner illustrated in FIG. 6 and, as in the fixator shown in FIG. 3, threadably engages a threaded bore in member 88. The planar members 88 and 94 are preferably formed of a moldable and steam autoclavable plastics material such as Delrin, and being of smaller size than those used in the embodiment of FIG. 1, it may be desirable, for added strength, to insert a threaded metal bushing in the bore in member 88. Planar members 88 and 94 are normally maintained in the same plane by the coaction of rod 96 and a second, smaller diameter, rod 98, one end of which is anchored, as by threading, in member 94, and the other end of which slides freely in a bore formed in member 88 in parallel off-set relationship with respect to rod 96. As in the other embodiment, the free end of rod 96 is squared off to have the same shape and size as the head of screws 90 and 92 (and others to be described) so as to be rotated by wheel 60 to effect longitudinal movement of member 88 relative to member 96. A square-headed screw 100 extends inwardly from the upper edge of member 88 through a threaded opening for locking member 88 to adjusted positions along rod 96. In the event the adjusted spacing between members 88 and 94 is sufficient to disengage rod 98 from the bore in member 88 thereby to allow relative rotation of members 88 and 94 on rod 96, screw 100, and a square-headed screw 102 which extends inwardly from the upper edge of member 94, are used to lock the two planar members in desired angularly adjusted positions.

The free ends of the other bone pins 78 and 80 extend through respective sleeves 104 and 106 provided in a third planar member 108 and clamped by respective square-headed screws 110 and 112. Planar member 108, which has the same cross-section and is formed of the same material as the other two members, is joined at one end to the distal end of member 94 by a tongue and groove hinge assembly so as to be angularly adjustable in the plane of member 108. In the illustrated embodiment, the hinge assembly comprises a tongue plate 114, preferably formed of stainless steel, secured in a slot in member 108 by suitable fastening means such as a pair of rivets 116, and a pair of plates 118 and 120 secured to opposite faces of member 94 such as by rivets 122 and spaced apart sufficiently to receive the tongue plate 114 between them with enough clearance to allow freedom of motion. The assembly is locked in a desired angularly adjusted position by a square headed screw 124 which passes through a hole in tongue plate 114 and engages a threaded hole in plate 120. The surfaces of tongue plate 114 are preferably roughened for preventing relative rotation of the parts when plates 118 and 120 are pressed against the planar surfaces of the tongue plate by tightening of the screw.

This fixture embodiment, too, may be also used as a drill guide for initially locating the bone pins. For example, after first inserting pin 76 (for example) into the radius, it may be inserted into sleeve 86, and after the two sections of the fixator are aligned to their approximate final positions with respect to the wrist, is clamped therein by screw 92, thereby to positin the fixator to permit its convenient use as a guide for inserting the other required pins. When applying the fixator, the axis of screw 124 is lined up with the wrist joint to allow dorsiflexion and volar-flexion. Reduction of the wrist joint is determined by the adjusted distance between pins 74, 76 inserted in the radius and pins 78, 80 inserted in the metacarpals. Relative ulnar positioning ("ulnar deviation") of the wrist is obtained by releasing screws 110 and 112, adjusting the length of the pins 78 and 80 between the metacarpals and member 108, and then clamping the pins to the newly adjusted length. It will be understood that increasing the spacing between the two pairs of bone pins puts tension across the fracture site and precludes shortening of the radius as the fracture heals. The spacing is conveniently adjustable as required during healing, and it is easy to achieve ulnar deviation, if desired.

FIG. 8 shows an alternative construction for the tongue and groove hinge assembly of the fixator shown in FIG. 7 which provides essentially the function of a universal joint at relatively lower cost. In this case, planar member 108' is joined at one end to the distal end of member 94 by an assembly consisting of a tongue 130 integral with and projecting from the end of member 94 to be received between the plates 132 and 134 of a groove assembly 136 which also includes an integral cylindrical rod 138 which is received in a longitudinally extending cylindrical bore formed in member 108'. The assembly is locked in a desired angularly adjusted position by a squareheaded screw 124' which passes through aligned holes in plate 132 and tongue plate 130 and engages a threaded hole in plate 134. The surfaces of tongue plate 130 and/or the inner surfaces of plates 132 and 134 may be roughened to insure against relative rotation of the members from the locked position. With the tongue and groove assembly locked at a desired angle, planar member 108' may be rotated about the long axis of rod 138 and locked in a desired rotationally adjusted position by a square-headed screw 140 which threadably engages a metal sleeve 142 which is either pressed or molded into the longitudinal bore in member 118'. Thus, the member 108' may be both angularly and rotationally adjusted relative to member 94' and member 88; it will be understood that the order in which the adjustments are made is a matter of choice determined by the fracture and the treatment required.

It will have become apparent that applicant has provided a fixator device which is easily manufactured from less expensive materials than are employed in prior art devices but which is sterilizable by conventional steam autoclaving; the pin-receiving sleeves, which may be standard commercially available drill guide bushings, are readily molded into the planar members, and the square-headed screws and required rod stock are readily available. The simple lead screw, which is integral with the planar members, not only gives the fixator strength and stability, but enables convenient and rapid adjustment. Finally, by virtue of all screw heads and the end of the lead screw being of the same shape and size, all operations involved in securing the fixator to the bone pins and adjusting the distraction/compression, are accomplished with a single, simple, easily manipulated tool, itself inexpensive to manufacture.

Although Delrin has proven to be an exemplary material for the fabrication of the planar members and the actuating tool, any polymer of sufficient strength which is both moldable and sterilizable in a steam autoclave may be used; examples include Nylon, carbon-filled polyethylene and fiberglass. And, although the invention has been described in detail as to preferred embodiments, it is obvious that certain modifications or alterations may be made thereto without departing from the spirit of the invention. For example, the tongue and the groove in both the FIG. 7 and FIG. 8 assemblies may be reversed, if desired and/or the tongue 114 in FIG. 7 may be an integral extension of member 108 and/or the tongue 130 in FIG. 8 may be formed of metal and secured in a groove in member 94 in the manner that tongue 114 is secured to member 108 in FIG. 7. The scope of the invention should thus be determined by the claims appended hereto.

I claim:

1. An external fixator for bridging a bone fracture for use with bone pins intended to be inserted in groups into the fracture fragments, said fixator comprising:

first and second elongated solid planar members formed of a moldable and/or machinable plastics material, said planar members being generally rectangular in shape and cross-section and having a width dimension greater than the thickness dimension, said planar members being arranged in end-to-end relationship in a common plane and each having openings therethrough transverse to its longitudal axis in the direction of the thickness dimension distributed along its length and disposed on a line displaced from one edge of the member by a distance less than half said width dimension for receiving and supporting the pins of a respective one of two groups of pins separate means associated with each of said openings for releasably clamping a pin therein comprising a screw extending inwardly from said one edge of the planar member into engagement with the pin, said screw having a head of predetermined shape and size, an elongated lead screw anchored at one end for relative rotation in said first planar member at the end thereof which confronts an end of said second planar member and extending completely through and projecting beyond the other end of said second planar member and threadably engaging a threaded longitudinal bore therein, said lead screw being disposed along an axis parallel to and displaced slightly inwardly from said line of openings and when rotated relative to said second planar member effecting an adjustment in distance between the confronting ends of said first and second planar members whereby to establish a definite extension of the fracture, the projecting end of said lead screw having the same shape and size as the heads of said clamping screws whereby a single tool having an opening of said predetermined shape and size can be used interchangeably to rotate said lead screw to effect said adjustment in distance or to actuate said clamping screws, and a rod secured at one end and in the end of said first planar member which confronts an end of said second planar member and slidably engaging a bore in said second planar member, the axis of which is parallel to and off-set from the axis of said lead screw for normally coacting with said lead screw to maintain said planar members in a common plane.

2. An external fixator as defined in claim 1, wherein each of said transverse openings is defined by a metal sleeve and each of said clamping screws threadably engages a respective sleeve, and said fixator further comprises a tool for interchangeably actuating said clamping screws or said lead screw, said tool comprising a wheel of a size to be hand-manipulated and having a central opening of said predetermined shape and size for receiving and engaging said free end of said lead screw.

3. An external fixator as defined in claim 2, wherein said first and second planar members each include a locking screw extending inwardly from said one edge and engaging said lead screw for locking adjusted relative longitudinal positions of said planar members.

4. An external fixator as defined in claim 2, wherein said first and second planar members and said tool are all formed of a plastics material which is machinable and/or moldable and sterilizable in a steam autoclave, and said lead screw, said rod, said sleeves and said screws are formed of a metal which is sterilizable in a steam autoclave.

5. An external fixator as defined in claim 2, wherein said first planar member comprises first and second articulated sections arranged for relative angular adjustment in said common plane and includes locking means actuable with said tool for locking said sections in angularly-adjusted positions.

6. An external fixator as defined in claim 5, wherein said one end of said lead screw is anchored in the first section of said articulated first member at the end thereof which confronts said second member, and the second section of said articulated first member has said transverse openings therethrough for supporting the pins of a respective group.

7. An external fixator as defined in claim 6, wherein the first section of said first planar member and said second planar member each have a locking screw extending inwardly from said one edge at a point thereon adjacent the end which confronts the other planar member and engaging said lead screw for locking adjusted relative longitudinal positions of said planar members.

8. An external fixator as defined in claim 5, wherein said fixator further includes means for enabling relative rotational adjustment of said first and second sections and locking means actuable with said tool for locking said first and second sections in relative rotationally-adjusted positions.

9. An external fixator as defined in claim 7, wherein said fixator further includes means for enabling relative rotational adjustment of said first and second sections and locking means actuable with said tool for locking said first and second sections in relative rotationally adjusted positions.

10. An external fixator as defined in claim 5, wherein said relative angular adjustment between said first and second sections of said first planar member is provided by a hinge assembly including a tongue disposed at the confronting end of one of said sections and engaging a groove structure disposed at the confronting end of the other of said sections.

11. An external fixator as defined in claim 10, wherein said groove structure includes an integral rod projecting into a cylindrical bore formed in the said other of said sections for rotation therein relative to said other of said sections, and wherein said fixator further includes locking means actuable with said tool for locking said sections in relative rotationally adjusted positions.

12. An external fixator as defined in claim 7, wherein said planar members and said tool are all formed of a plastics material which is machinable and/or moldable and steam sterilizable in a steam autoclave, and said lead screw, said rod, said locking means and said screws are formed of a metal which is sterilizable in a steam autoclave.

13. An external fixator as defined in claim 9, wherein said planar members and said tool are all formed of a plastics material which is steam sterilizable in a steam autoclave, and said lead screw, said rod, said locking means and said screws are formed of a metal which is sterilizable in a steam autoclave.

14. An external fixator as defined in claim 2, wherein said plastics material is Delrin and said metal is stainless steel.

* * * * *